(12) United States Patent
Munson

(10) Patent No.: US 10,092,545 B2
(45) Date of Patent: Oct. 9, 2018

(54) NUTRITIONAL SUPPLEMENTS FOR IMPROVING FEMALE FERTILITY

(71) Applicant: Fairhaven Health, LLC, Bellingham, WA (US)

(72) Inventor: Suzanne Munson, Bellingham, WA (US)

(73) Assignee: Fairhaven Health, LLC, Bellingham, WA (US)

(*) Notice: Subject to any disclaimer, the term of this patent is extended or adjusted under 35 U.S.C. 154(b) by 87 days.

(21) Appl. No.: 15/143,546

(22) Filed: Apr. 30, 2016

(65) Prior Publication Data

US 2017/0312251 A1    Nov. 2, 2017

(51) Int. Cl.

| | | |
|---|---|---|
| A61K 38/43 | (2006.01) | |
| A61P 15/08 | (2006.01) | |
| A61K 31/122 | (2006.01) | |
| A61K 31/015 | (2006.01) | |
| A61K 31/195 | (2006.01) | |
| A61K 31/4045 | (2006.01) | |
| A61K 31/047 | (2006.01) | |
| A61K 31/198 | (2006.01) | |
| A61K 31/375 | (2006.01) | |
| A61K 31/593 | (2006.01) | |
| A61K 31/355 | (2006.01) | |
| A61K 31/51 | (2006.01) | |
| A61K 31/525 | (2006.01) | |
| A61K 31/455 | (2006.01) | |
| A61K 31/4415 | (2006.01) | |
| A61K 31/519 | (2006.01) | |
| A61K 31/714 | (2006.01) | |
| A61K 31/4188 | (2006.01) | |
| A61K 33/26 | (2006.01) | |
| A61K 33/18 | (2006.01) | |
| A61K 33/30 | (2006.01) | |
| A61K 33/24 | (2006.01) | |
| A61K 33/34 | (2006.01) | |
| A61K 33/32 | (2006.01) | |
| A61K 31/385 | (2006.01) | |
| A61K 31/14 | (2006.01) | |
| A61K 31/05 | (2006.01) | |
| A61K 31/675 | (2006.01) | |
| A61K 36/87 | (2006.01) | |
| A23L 1/30 | (2006.01) | |
| A23L 1/302 | (2006.01) | |
| A23L 1/304 | (2006.01) | |
| A23L 1/29 | (2006.01) | |
| A23L 33/00 | (2016.01) | |

(52) U.S. Cl.
CPC .......... *A61K 31/4045* (2013.01); *A23L 1/296* (2013.01); *A23L 1/30* (2013.01); *A23L 1/3002* (2013.01); *A23L 1/302* (2013.01); *A23L 1/304* (2013.01); *A23L 33/00* (2016.08); *A61K 31/015* (2013.01); *A61K 31/047* (2013.01); *A61K 31/05* (2013.01); *A61K 31/122* (2013.01); *A61K 31/14* (2013.01); *A61K 31/195* (2013.01); *A61K 31/198* (2013.01); *A61K 31/355* (2013.01); *A61K 31/375* (2013.01); *A61K 31/385* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/675* (2013.01); *A61K 31/714* (2013.01); *A61K 33/18* (2013.01); *A61K 33/24* (2013.01); *A61K 33/26* (2013.01); *A61K 33/30* (2013.01); *A61K 33/32* (2013.01); *A61K 33/34* (2013.01); *A61K 36/87* (2013.01); *A61P 15/08* (2018.01); *A23V 2002/00* (2013.01)

(58) Field of Classification Search
CPC .............. A61K 31/122; A61K 31/4045; A61K 31/015; A61K 31/195; A61P 15/08
See application file for complete search history.

(56) References Cited

PUBLICATIONS

TTC Boost Bundle for Her. Datasheet [online]. Fairhaven Health, Feb. 15, 2015 [retrieved on Dec. 20, 2017]. Retrieved from the Internet: <URL: https://web.archive.org/web/20150215141357/http://www.fairhavenhealth.com:80/ttc-boost-bundle.html>.*

Nordio, M. and Proietti, E., The combined therapy with myo-inositol and D-chiro-inositol reduces the risk of metabolic disease in PCOS overweight patients compared to myo-inositol supplementation alone. European Review for Medical and Pharmacological Sciences, vol. 16 (2012) pp. 575-581.*

Salehpour et al., N-acetylcysteine as an adjuvant to clomiphene citrate for successful induction of ovulation in infertile patients with polycystic ovary syndrome. The Journal of Obstetrics and Gynaecology Research, vol. 38, No. 9 (Sep. 2012) pp. 1182-1186.*

* cited by examiner

*Primary Examiner* — Kara D Johnson

(74) *Attorney, Agent, or Firm* — Don D. Cha; Hamilton DeSanctis & Cha, LLP

(57) ABSTRACT

The present invention relates to a fertility-enhancing composition for human male fertility therapy and a method for using the same to improve or enhance human male fertility. The nutritional supplement composition of the invention includes an effective amount of L-carnitine tartrate, coenzyme Q10, methylcobalamin, N-acetyl L-cysteine, and grape seed extract.

11 Claims, No Drawings

NUTRITIONAL SUPPLEMENTS FOR IMPROVING FEMALE FERTILITY

FIELD OF THE INVENTION

The present invention relates to a fertility-enhancing composition for human female fertility therapy and a method for using the same to improve human female fertility.

BACKGROUND OF THE INVENTION

Female eggs in mammals are constantly subjected to stresses from physical, chemical, and biological sources that can result in conception problems due at least in part to poor or insufficient egg quality and or ovarian function. These problems may be compounded in the cases of female humans not receiving sufficient amount of nutrients.

Attempts to improve egg quality can be hampered in the case where female human is under nourished or malnourished, thereby resulting in lack of requisite building blocks to promote oogenesis, i.e., egg production. Oogenesis results in the formation of a large cell having a variety of resources for the construction of the embryo. Thus, oogenesis requires a sufficient amount of various nutrients to provide the cellular building blocks to create proper cells. Some of the basic cellular building blocks include, but are not limited to, amino acids, carbohydrates, proteins, vitamins, minerals, and other nutrients.

Conventional treatments for female human infertility conditions include the administration of various hormones, such as human menopausal gonadotrophin (hMG) (consisting of equal amounts of follicle stimulating hormone, FSH, and luteinizing hormone LH), or luteinizing hormone releasing hormone (LHRH). Treatment with these hormones however, is generally expensive, and does not always yield satisfactory results. Moreover, in some cases, hormone therapy results in various undesired side-effects.

Therefore, there is a need for improving female egg quality, ovarian function, and overall female fertility without the use of hormone therapy.

SUMMARY OF THE INVENTION

The present invention provides a nutritional supplement composition for improving female fertility. Without being bound by any theory, it is believed that the composition of the invention is believed to be particularly useful in improving female fertility where the cause of female infertility is at least due in part to oxidative stress.

The nutritional supplement composition of the invention comprises various components in a single unit. In one aspect of the invention, nutritional supplement composition of the invention for improving female fertility comprises an effective amount of myo-inositol, d-chiro-inositol, melatonin, n-acetyl 1-cysteine and coenzyme Q10.

Yet in other embodiments, the single unit of the composition of the invention further comprises an antioxidant, vitamins, minerals or a combination thereof.

Still yet in other embodiments, the single unit of the composition of the invention further comprises a α-lipoic acid, grape seed extract, trans-resveratrol, or a combination thereof.

Another aspect of the invention provides a method for improving egg quality, ovarian function, and/or overall female fertility in a female human. Such a method typically comprises administering to a female human an effective amount of a composition of the invention.

DETAILED DESCRIPTION OF THE INVENTION

Some aspects of the invention provide a single unit composition for improving female infertility without using a hormone therapy. The effects of the components of the composition of the invention have been shown by various researchers, but never before has a composition been provided that enhances or increases female infertility that is believed to be at least due in part to oxidative stress.

In the following description, numerous specific details are set forth in order to provide a more thorough description of the present invention. It will be apparent, however, to one skilled in the art, that the present invention may be practiced without these specific details. Moreover, it is to be understood that the present disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally. In this manner, a wide variety of combination of embodiments and aspects of the invention are possible.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm. The term "about" when referring to a number refers to ±20%, typically ±10%, and often ±5% of the numeric value. The term "or" is used herein as a conjunction used to link alternatives in a series of alternatives. The term "and/or" is used herein as a conjunction meaning that either or both of two options may be valid. The term "conception" refers to the beginning of pregnancy as marked by the formation of a zygote. "Possibility of conception" refers to the likelihood of conception occurring during normal sexual activity.

One aspect of the invention provides a composition for improving human female fertility. The composition may be in a dosage form of a tablet, capsule, liquid, liposome, inhalant, sublingual tablet, suppository, oral spray and dermal patch and may further comprise a pharmaceutically acceptable carrier. As used herein, the term "improving human female fertility" refers to a statistically significant increase in human female fertility by at least about 5%, typically by at least about 10%, often by at least about 25%, more often by at least about 30%, and most often by at least about 50% resulting from administration of a composition of the invention. The improvement in female fertility can be measured, for example, by a typical experimental procedure known to one skilled in the art in determining efficacy of a nutritional supplement. One frequently used method involves administering a composition of the invention to a group of female individuals (i.e., "test group") and administering a placebo composition to another group of female individuals (i.e., "control group"). By comparing the fertility efficacy between the test group and the control group, one can determine the efficacy of a composition of the invention in improving female fertility.

In some embodiments, the control group and the test group are selected by matching one or more characteristics, such as age, race, or any relevant biological or sociological factor that may affect the control group and the test group (e.g., preexisting conditions, consumption of particular substances such as alcohol, levels of other biological or physiological factors). The number of matched individuals from whom control group must be obtained to establish a suitable control level (e.g., a population) can be determined by those of skill in the art, but should be statistically appropriate to establish a suitable "baseline" or control data for comparison with the test group to be evaluated. The values obtained from the control group and the test group are statistically processed using any suitable method of statistical analysis to establish a suitable comparative data using methods standard in the art.

Improvement in egg quality due to using a composition of the invention can be determined, for example, by comparing the egg quality of the female subject prior to being on the regiment of taking the composition of the invention and after being on the nutritional supplement regiment for a given period of time, e.g., one month, two months, three months, four months, five months, six months, etc.

Methods of improving female fertility include administering the composition of the invention to a female subject for a period of time sufficient to improve female fertility. In some embodiments, compositions of the invention include comprehensive vitamins and minerals to provide antioxidant protection and/or to improve egg quality. The ingredients in the composition of the invention have shown to promote female fertility and overall reproductive health by decreasing oxidative stress, improving nutritional status, and/or improving the quality of egg and/or ovarian function. Typically, the female subject begins taking the composition of the invention at least one month, typically at least two month, and often three to six months before trying to conceive naturally or initiating assisted reproductive technologies (e.g., in vitro fertilization).

Some of the benefits of the composition of the invention include, but are not limited to, formulated to meet standards recommended by fertility experts, designed to be used in conjunction with assisted reproductive technologies, provides effective dosages of key fertility-enhancing ingredients, including myo-inositol, d-chiro-inositol, melatonin, n-acetyl 1-cysteine and coenzyme Q10.

Still in other embodiment, the composition further comprises an antioxidant, vitamins, minerals or a combination thereof.

Yet still in other embodiments, the composition further comprises α-lipoic acid, grape seed extract, trans-resveratrol, or a combination thereof It should be appreciated that combination of various combinations of components described herein form other embodiments. In this manner, a variety of compositions are embodied within the present invention.

The term "single serving size" may not be synonymous with the term "single dose" or "single unit" or "single dosage form". The term "single serving size" refers to a recommended amount of intake per day or 24 hour period. Thus, the term "single serving size" generally refers to the amount of a given component provided to female human in a given day by compositions of the invention. While the "single serving" reflects the total daily amount, it may be administered in portions throughout the day. Thus, the amount of "single serving size" simply refers to the amount of a given component of the composition of the invention that is provided in a given day or within about a 24 hour period. In contrast, the term "single unit," "single dose," or "single dosage form," which unless context requires otherwise are used interchangeably herein, refer to a single solid or solution form containing all of the described ingredients. While some conventional nutritional supplements contain various components in different solid or solution forms to make-up one serving size, the single unit nutritional supplements of the invention include all of the components in one unit, e.g., one single solid form or one single vial of solution. That is, all of the components are present together as a unit.

Antioxidants play an important role in protecting eggs from reactive oxygen species ("ROS") or oxidative stress. Administration of antioxidants to female humans improves egg quality, ovarian function and/or improves female fertility. Thus, in some embodiments compositions of the invention include an array of antioxidant nutrients, including but not limited to, coenzyme Q10, vitamin E, and α-lipoic acid, to protect egg cells from the damaging effects of age and environmental toxins. Still in other embodiments, compositions of the invention also include full preconception vitamin support, as well as myo-inositol and d-chiro inositol to promote hormone balance, insulin sensitivity, and ovarian function. Still in other embodiments, a significant improvement in female fertility is achieved by administering the composition of the invention from about three to about six months before trying to conceive naturally or initiating assisted reproductive technologies, e.g., in vitro fertilization.

Compositions of the invention can be used by women to increase the likelihood or probability of natural or assisted conception. In some embodiments, compositions of the invention comprise ingredients in amounts that have been shown to be safe and effective, based on the current understanding of female fertility. In particular, compositions of the invention include ingredients that have been shown to improve egg health and ovarian function. Accordingly, it is believed that compositions of the invention can significantly increase female fertility compared to the control group. In some embodiments, compositions of the invention also include multivitamins that have shown to be necessary for female health.

In some embodiments, compositions of the invention are particularly useful for females suffering from polycystic ovary syndrome ("PCOS") as well as those of advanced maternal age. PCOS is associated with hormone imbalance, and results in a variety of symptoms, one of which is impaired fertility. While there are a variety of symptoms due to PCOS, one of the clinical conditions associated with PCOS is difficult to in achieving pregnancy. Without being bound by any theory, it is believed that by providing nutrients that promote hormonal balance in women, compositions of the invention can increase fertility in women suffering from PCOS.

In some embodiments, the composition of the invention comprises antioxidants as well as other nutrients that are beneficial to female fertility. For example, in one embodiment, compositions of the invention include an array of antioxidant nutrients, including CoQ10, vitamin E, and α-lipoic acid, to protect egg cells from the damaging effects of age and environmental toxins. Compositions of the invention can also include preconception vitamin support, along with myo-inositol and d-chiro inositol to promote hormone balance, insulin sensitivity, and ovarian function.

The ratio of myo-inositol ("MI") and d-chiro inositol ("DCI") can vary. However, for improving female fertility in those suffering from PCOS, the ratio of MI to DCI is typically from about 30:1 to about 50:1, often from about 35:1 to about 45:1, and most often about 40:1. However, it should be appreciated that the scope of the invention is not limited to MI:DCI ratios described herein. Any ratio of MI:DCI can be used depending on a particular individual female's needs or desired clinical achievements.

Some of the ingredients present in compositions of the invention are discussed below along with some of the benefits of such ingredients. The amount of each ingredients disclosed herein refers to a single serving size. The amount of single unit that is administered to female human depends on the size of the single unit. However, typically a single unit is formulated such that three, typically four, often five or more often six single units make up a single serving size.

Coenzyme Q10 ("CoQ10") is believed to improve fertility particularly in females of advanced maternal age. The term "advanced material age" refers to female humans who are about thirty-five years of age or older. For example, one study concluded that "Ovarian reserve in the oocyte-specific Pdss2-deficient animals was diminished, leading to premature ovarian failure which could be prevented by maternal dietary administration of CoQ10." Ben-Meir et al., *Aging Cell.*, 2015, 14(5), pp. 887-895. This study concluded that "impaired mitochondrial performance created by suboptimal CoQ10 availability can drive age associated oocyte deficits causing infertility." Thus, it is believed by providing a sufficient amount of CoQ10, compositions of the invention can improve or increase fertility in female humans. Without being bound by any theory, it is believed that CoQ10 as an antioxidant helps with cellular energy production and prevents premature ovarian failure, as well as reduces effects of reproductive aging. The amount of CoQ10 provided in a single serving size of compositions of the invention is at least about 150 mg, typically at least about 250 mg, and often at least about 300 mg.

Compositions of the invention can also include vitamin D. This is based on a study that showed "In women undergoing in-vitro fertilization, a sufficient vitamin D level (greater than or equal to 30 ng/ml) should be obtained." Lerchbaum et al., *Curr Opin Obstet Gynecol.*, 2014, 26(3), 145-50. Thus, a single serving size of compositions of the invention includes at least about 2,000 IU, typically at least about 2,500 IU and often at least about 2,800 IU of vitamin D.

Some studies have shown beneficial effects of melatonin on female fertility. For example, a study by Tamura et. al. in the *Endocrine Journal*, 2013, 60(1), 1-13, concluded " . . . clinical study demonstrated that melatonin treatment for infertile women increases intra-follicular melatonin concentrations, reduces intra-follicular oxidative damage, and elevates fertilization and pregnancy rates." Accordingly, a single serving size of compositions of the invention can also include at least about one mg, often at least two mg of melatonin.

In other embodiments, vitamin A (e.g., as beta-carotene) can also be present in compositions of the invention. Beta-carotene is a known antioxidant, and Vitamin A provides prenatal nutritional support. It also provides prenatal nutritional support. The presence of vitamin A also improves in vitro fertilization outcomes when used in conjunction with other antioxidants. The amount of vitamin A present in a single serving size of a composition of the invention is at least about 2,000 IU, typically at least about 3,000 IU, often at least about 4,000 IU and more often at least 5,000 IU.

Vitamin C (as ascorbic acid). Vitamin C is also a known antioxidant. It too provides prenatal nutritional support. The presence of vitamin C compositions of the invention also improves in vitro fertilization outcomes when used in conjunction with other antioxidants. The amount of vitamin C present in a single serving size of a composition of the invention is at least about 50 mg, typically at least about 100 mg, often at least about 200 mg and more often at least 240 mg.

As discussed above, vitamin D inter alia improves rate of success in assisted reproductive technologies. The amount of vitamin D in a single serving size of compositions of the invention includes at least about 2,000 IU, typically at least about 2,500 IU and often at least about 2,800 IU of vitamin D.

Vitamin E is also a known antioxidant. In some embodiments of the invention, vitamin E is present in the composition 75% as d-α-tocopheryl succinate and 25% as mixed tocopherols. In other embodiments, vitamin E is present in the composition 87.5% as d-α-tocopherol. Without being bound by any theory, vitamin E promotes egg quality, i.e., improves egg quality, thereby increasing female fertility. In addition, it is believed that the presence (i.e., regular administration) of vitamin E significantly improves pregnancy and live birth rates in couples undergoing assisted reproductive technologies, especially when used in conjunction with other antioxidants. The amount of vitamin E present in a single serving size of a composition of the invention is at least about 25 IU, typically at least about 50 IU, often at least about 75 IU and more often at least about 100 IU.

Vitamin K (e.g., 50% as K1 and 50% as K2) is an essential nutrient for general overall health of humans. For example, vitamin K has been shown to be important for heart and bone health. Dietary deficiency of vitamin K is common. The amount of vitamin K present in a single serving size of a composition of the invention is at least about 40 mcg, typically at least about 50 mcg, often at least about 60 mcg and more often at least 80 mcg.

In some embodiments, compositions of the invention also include thiamin (e.g., as thiamine hydrochloric acid salt and/or benfotiamine). The amount of thiamine present in a single serving size of compositions of the invention is about 1 mg, typically at least 2 mg and often at least 3 mg. Benfotiamine is a lipid-soluble form of thiamine. It has shown to be effective metabolic precursor of active thiamine. The presence of benfotiamine in compositions of the invention helps ensure thiamine levels are sufficient and prevents damage by oxidative stress.

Compositions of the invention can also include riboflavin. When present, riboflavin is typically present as riboflavin 5 phosphate. The amount of riboflavin present in a single serving size of compositions of the invention is at least about 1 mg, typically at least about 2 mg and often at least about 3.4 mg.

Yet in other embodiments, compositions of the invention can also include niacin, e.g. as niacinamide. When present, the amount of niacin present in a single serving size of compositions of the invention is at least about 10 mg, typically at least about 20 mg, often at least about 30 mg and most often at least about 40 mg.

In some embodiments, compositions of the invention also include vitamin B6. When present, the amount of vitamin B6, typically as pyridoxal 5 phosphate, in a single serving size comprises at least about 1 mg, typically at least about 2 mg, often at least about 3 mg and most often at least about 4 mg.

B9/Folate (e.g., as QUATREFOLIC® (glucosamine salt of (6S)-5-methyltetrahydrofolate)) is also a known antioxidant. Studies have shown that the presence of folate prevents neural tube defects. Folate is also important for oocyte quality, maturation, implantation, placentation, fetal growth and organ development. In addition, folate can counteract harmful effects of reactive oxygen species ("ROS"). In some studies, administration of folate has shown to significantly improve pregnancy rates. The amount of folate present in a single serving size of compositions of the invention is at least about 200 mcg, typically at least about 400 mcg, often at least about 600 mcg and most often at least about 800 mcg.

Vitamin $B_{12}$ (e.g., as methylcobalamin) is involved in cellular replication. Therefore, in some embodiments, compositions of the invention include vitamin $B_{12}$. Typically, the amount of vitamin $B_{12}$ in a single serving size of compositions of the invention is at least about 6 mcg, typically at least about 8 mcg, often at least 10 mcg and most often at least 12 mcg.

Still in other embodiments, compositions of the invention can also include biotin (e.g., as d-biotin). When present, the amount of biotin in a single serving size of compositions of the invention is at least about 200 mcg, typically at least about 400 mcg and often at least about 600 mcg.

Another ingredient that can be included in compositions of the invention is pantothenic acid (e.g., as a calcium salt). When present, the amount of pantothenic acid present in a single serving size of compositions of the invention is at least about 5 mg, typically at least about 10 mg, often at least about 15 mg and most often at least about 20 mg.

Iodine (e.g., as potassium iodide) is necessary for the production of thyroid hormones which in turn affects female fertility. Insufficient level of iodine can impact female fertility. In addition, iodine is important for fetal brain development. It should be noted with modern diet, iodine deficiency is becoming increasingly common. Thus, in some embodiments, compositions of the invention also include iodine. Typically the amount of iodine in a single serving size of compositions of the invention is at least about 50 mcg, typically at least about 100 mcg and often at least about 150 mcg.

Zinc (e.g., as zinc citrate) is important for sexual development, ovulation, and menstrual cycle regulation. Zinc has also been shown to act as an antioxidant that counteracts ROS. Without being bound by any theory, it is believed that the presence of zinc significantly improves pregnancy rate. It also increases live birth rate. In particular, improvement in live birth rate of men/couples undergoing assisted reproductive technology is observed when used in conjunction with other antioxidants. When present, the amount of zinc in a single serving size of compositions of the invention is at least about 10 mg, typically at least about 20 mg and often at least about 30 mg.

Selenium is also a known antioxidant. Selenium protects egg cells in the late stages of follicle development. Use of selenium has been shown to significantly increase pregnancy rates, as well as improve live birth rates, especially in assisted reproductive technologies when used in conjunction with other antioxidants. Accordingly, compositions of the invention can also include selenium, typically as selenomethionine. When present, the amount of selenium in a single size serving of compositions of the invention is at least about 30 mcg, typically at least about 50 mcg and often at least about 70 mcg.

Copper has been shown to participate in as an electron donor in biological reactions. Thus, it is believed it can counteract effects of reactive oxygen species. Compositions of the invention can also include copper, e.g., as copper sulfate. When present, the amount of copper in a single size serving of compositions of the invention is at least about 1 mg.

Manganese is an essential mineral for enzymes that protect the mitochondria from reactive oxygen species and other free radicals. Thus, the presence of manganese is believed to reduce female infertility due to oxidative stress. Accordingly, in some embodiments, compositions of the invention also include manganese, typically as manganese bisglycinate chelate. When present, the amount of manganese in a single size serving of compositions of the invention is at least about 1 mg and often at least about 2 mg.

Chromium has been shown to help regulate sugar metabolism by working with insulin. In fact, it has been shown that the presence of chromium enhances the action of insulin. Moreover, some studies suggest administering chromium for as little as two months improves insulin sensitivity by more than 30% in obese women with PCOS. Accordingly, it is believed that chromium is particularly useful for improving fertility in females with PCOS. Thus, in some embodiments, compositions of the invention include chromium as chromium polynicotinate. When present, the amount of chromium in a single serving size of compositions of the invention is at least about 150 mcg, typically at least about 200 mcg and often at least about 240 mcg.

Molybdenum is essential for virtually all life forms. It has been shown that molybdenum helps conversion of sulfur into a useable form in the body. Accordingly, the presence of molybdenum improves overall general health of human, including the fetus. Thus, compositions of the invention can also include molybdenum. Typically molybdenum is present as molybdenum glycinate chelate. When present, the amount of molybdenum in a single size serving of compositions of the invention is at least about 25 mcg, typically at least about 50 mcg and often at least about 75 mcg.

Some compositions of the invention also include iron, e.g., as iron glycinate. Iron is necessary for healthy pregnancy and is needed for hemoglobin synthesis. Iron is also a component of myoglobin, collagen and many enzymes. Iron has also been shown to participate in immune function. Iron is particularly important for women, due to loss of blood during menstrual cycle. Thus, in some embodiments, compositions of the invention include iron. In general, a single serving size of compositions of the invention include at least about 10 mg, typically at least about 12 mg, often at least about 15 mg and most often at least about 18 mg of iron.

It has been shown that even mild elevations in blood sugar and insulin can negatively impact fertility in all women who are trying to conceive (i.e., "TTC women"), not just those with PCOS. Polycystic ovary syndrome is one of the most common causes of chronic anovulation infertility in women. As stated previously, PCOS is due to imbalance in hormones, namely increased production of androgens and estrogens. Some studies have shown that females taking myo-inositol had decreased serum testosterone level and increased insulin sensitivity. In general, women undergoing in vitro fertilization who are given myo-inositol experience an overall improvement in the ovulatory function, as well as improved quality and quantity of oocytes. See, for example, Ciotta et al., *Eur. Rev. Med. Pharmacol. Sci.*, 2011, 15(5), 509-14. Accordingly, compositions of the invention include myo-inositol. Without being bound by any theory, it is believed that in the composition of the invention, the amount of myo-inositol is sufficient to help reduce insulin resistance in women with PCOS but also sufficient to improve egg quality. The amount of myo-inositol present in a single serving size of compositions of the invention is at least about 500 mg, typically at least about 1000 mg, often at least about 1500 mg and most often at least about 2000 mg.

In addition to myo-inositol, d-chiro-inositol can also improve insulin sensitivity, ovulation, and serum androgen levels in female humans. In one particular study, it has been found that physiologic ratio of MI:DCI of about 40:1 provided the most significant reduction in risk of metabolic disease in PCOS overweight patients as well as improved IVF outcomes. Accordingly, the ratio of MI:DCI in compositions of the invention are those described above.

N-Acetyl L-cysteine (i.e., "NAC") improves live birth rate particularly those undergoing assisted reproductive technologies. NAC is also an antioxidant and is believed to be a precursor to glutathione. That is NAC is believed to be converted in vivo to glutathione ("GSH") and because oral glutathione is not metabolized well in small intestine, NAC is used to increase GSH levels. It has been shown that increased GSH improves IVF outcomes. In addition, the presence of NAC in compositions of the invention increases ovulation and increases chance of pregnancy in PCOS, particularly in women taking CLOMID® (clomiphene). The amount of N-acetyl L-cysteine present in a single serving size of compositions of the invention is at least about 25 mg, typically at least about 30 mg, often at least about 40 mg and most often at least about 50 mg.

Grape Seed Extract is a well known antioxidant. Various animal studies have shown grape seed extract comprising at least 80%, typically at least 85% polyphenols are effective in protecting against reproductive toxicity due to oxidative stress. In some embodiments, compositions of the invention include grape seed extracts that have at least about 80%, typically at least about 85% polyphenols. The amount of grape seed extract present in a single size serving of compositions of the invention is at least about 25 mg, typically at least about 30 mg, often at least about 40 mg and most often at least about 50 mg.

α-Lipoic acid is a water-soluble and fat-soluble antioxidant. Studies have shown α-lipoic acid can improve egg maturation and embryo viability. Thus, in some embodiments a single serving size compositions of the invention include at least about 25 mg, typically at least about 50 mg, often at least about 75 mg and most often at least about 100 mg of α-lipoic acid.

High homocysteine levels are associated with cardiovascular disease and miscarriage. In addition, high homocysteine levels are also associated with poorer egg and embryo quality in women. Accordingly, in some embodiments, compositions of the invention also include choline (e.g., as choline bitartrate). Choline is an essential nutrient that is produced in vivo in minute amounts. Choline is converted to betaine in the body, which assists in the conversion of homocysteine to methionine. This conversion prevents elevated homocysteine levels and provides better egg and embryo quality. A single serving size of composition of the invention includes at least about 10 mg, typically at least about 25 mg, often at least about 40 mg and often at least about 50 mg of choline.

In addition to grape seed extract which contains some amount of resveratrol, compositions of the invention can also include additional trans-resveratrol, e.g., from *Polygonum cuspidatum* root extract. Trans-resveratrol has been shown to protect cells from oxidative damage, protect mitochondrial function and enhance telomerase activity. Animal studies also show a favorable impact on both egg quality and quantity. A single serving size of composition shown in the invention includes at least about 10 mg, typically at least about 25 mg, often at least about 40 mg and often at least about 50 mg of trans-resveratrol.

Typically, compounds of the invention are administered as nutritional supplement formulations suitable for oral administration. However, it should be appreciated that the scope of the invention is not limited to such a mode of administration. Typical manner of administration is generally oral using a convenient daily dosage regimen (e.g., "single serving amount") that can be adjusted according to the unit dosage (i.e., "single unit") formulation.

Compositions of the invention, together with one or more conventional adjuvants, carriers, or diluents, can be placed into the form of nutritional supplement compositions and unit dosages. The nutritional supplement compositions and unit dosage forms can be comprised of conventional ingredients in conventional proportions, with or without additional active components or principles, and the unit dosage ("single unit") forms can contain any suitable effective amount of the desired components commensurate with the intended daily dosage range to be employed. The nutritional supplement compositions can be employed as solids, such as tablets or filled capsules, semisolids, powders, sustained release formulations, or liquids such as solutions, suspensions, emulsions, elixirs, or filled capsules for oral use.

The compositions of the invention can be formulated in a wide variety of oral administration dosage forms. The nutritional supplement compositions and dosage forms can comprise a various components of the invention. The pharmaceutically acceptable carriers can be either solid or liquid. Solid form preparations include powders, tablets, pills, capsules, cachets and dispersible granules. A solid carrier can be one or more substances that can also act as diluents, flavoring agents, solubilizers, lubricants, suspending agents, binders, preservatives, tablet disintegrating agents, or an encapsulating material. In powders, the carrier generally is a finely divided solid that is mixed with the finely divided components of the invention. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the composition of the invention with encapsulating material as carrier, providing a capsule in which the composition of the invention, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the composition of the invention in water and adding suitable colorants, flavors, stabilizers, and thickening agents. Aqueous suspensions can be prepared by dispersing the finely divided composition of the invention in water with viscous material, such as natural or synthetic gums, resins, methylcellulose, sodium carboxymethylcellulose, and other well known suspending agents. Solid form preparations include solutions, suspensions, and emulsions, and can contain, in addition to the composition of the invention, colorants, flavors, stabilizers, buffers, artificial and natural sweeteners, dispersants, thickeners, solubilizing agents, and the like.

When desired, the composition of the invention can be formulated with enteric coatings adapted for sustained or controlled release administration of the composition of the invention.

The composition of the invention is typically in unit dosage forms. As discussed in detail herein, a single serving can include more than one unit dosage form of compositions of the invention. For example, a single serving size can comprise two, three, four, five or six or more unit dosage forms. In such form, the preparation is often subdivided into unit doses containing appropriate quantities of the compositions of the invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Preparation of a Single Unit of a Composition of the Invention

Nutritional supplement capsules were produced using a conventionally known process. A single serving consisting of 6 capsules, i.e., each unit of capsule constituted ⅙ of daily recommended dosage of various components. Nutritional supplements were formulated such that 6 capsules (i.e., a single serving size) had the following quantities of compositions of the invention: β-carotene (5000 IU), ascorbic acid (240 mg), cholecalciferol (2800 IU), vitamin E (100 IU), vitamin K (80 mcg), thiamin (3 mg), riboflavin (3.4 mg), niacin (40 mg), vitamin B6 (4 mg), folate (800 mcg), vitamin $B_{12}$ (12 mcg), biotin (600 mcg), pantothenic acid (20 mg), iron (18 mg), iodine (150 mcg), zinc (30 mg), selenium (70 mcg), copper (1 mg), manganese (2 mg), chromium (240 mcg), molybdenum (75 mcg), myo-inositol (2000 mg), coenzyme Q10 (300 mg), α-lipoic acid (100 mg), choline (50 mg), d-chiro-inositol (50 mg), grape seed extract (50 mg), trans-resveratrol (50 mg), N-acetyl L-cysteine (50 mg), melatonin (2 mg) and benfotiamine (1 mg). Capsules also contained emulsifiers and binders such as vegetable capsule, microcrystalline cellulose, magnesium stearate and silicon dioxide.

Example 2

Efficacy

A control group of females and a test group of females, all of whom are having difficulty conceiving, are selected for testing. Each group is then further divided based on ethnicity and age range. Groups can be further subdivided based on a use of any similar medication, presence of any disease (e.g., diabetes), body mass index, similar alcohol consumption, and other factors. Control group is given placebo and the test group is given the nutritional supplement of Example 1. The rate of conception is followed each month for a year and is separated by in vitro fertilization or "natural" conception. The result is expected to show the test group receiving nutritional supplement of Example 1 will show higher rate of conception compared to the control group. It is expected the test group will show at least 5%, typically at least 10% and often at least 20% improvement in conception rate compared to the control group.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A single unit nutritional supplement composition for improving female fertility comprising an effective amount of a combination of myo-inositol, d-chiro-inositol, melatonin, n-acetyl l-cysteine, Resveratrol, Choline, Benfotiamine, and coenzyme Q10.

2. The nutritional supplement composition of claim 1, wherein the ratio of myo-inositol to d-chiro-inositol is about 40:1.

3. The nutritional supplement composition of claim 1, wherein said single unit nutritional composition further comprises an antioxidant, vitamins, minerals or a combination thereof.

4. The nutritional supplement composition of claim 1, wherein said single unit nutritional composition further comprises α-lipoic acid, grape seed extract, trans-resveratrol or a combination thereof.

5. The nutritional supplement composition of claim 1, wherein said single unit nutritional composition comprises at least 25 mg of N-acetyl L-cysteine.

6. The nutritional supplement composition of claim 1, wherein a single serving of said single unit nutritional composition comprises at least 50 mg of N-acetyl L-cysteine.

7. The nutritional supplement composition of claim 1 further comprising iron, selenium, zinc, copper, manganese, chromium, molybdenum, boron, choline bitartrate, or a combination thereof.

8. The nutritional supplement composition of claim 1 further comprising vitamin A, vitamin C, vitamin D3, vitamin E, vitamin K, thiamin, riboflavin, niacin, vitamin $B_6$, glucosamine salt of (6S)-5-methyltetrahydrofolate, vitamin $B_{12}$, pantothenic acid, biotin, iodine or a combination thereof.

9. A method for improving egg quality, ovarian function, overall female fertility or a combination thereof in a female human comprising administering to a female human an effective amount of a composition of claim 1.

10. The method of claim 9, wherein said composition is administered one to six unit dosage formulation per day to said female human.

11. The method of claim 9, wherein said composition is administered to said female human for at least 3 months prior to conception.

* * * * *